(12) United States Patent
Shi et al.

(10) Patent No.: US 9,671,364 B2
(45) Date of Patent: Jun. 6, 2017

(54) METHODS AND APPARATUS FOR RAPID DETECTION OF INFECTIOUS MICROORGANISMS

(71) Applicant: Becton, Dickinson and Company, Franklin Lakes, NJ (US)

(72) Inventors: Song Shi, Reisterstown, MD (US); James G. Nadeau, Ellicott City, MD (US); Michael A. Brasch, Gaithersburg, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/367,549

(22) PCT Filed: Dec. 19, 2012

(86) PCT No.: PCT/US2012/070538
§ 371 (c)(1),
(2) Date: Jun. 20, 2014

(87) PCT Pub. No.: WO2013/096404
PCT Pub. Date: Jun. 27, 2013

(65) Prior Publication Data
US 2015/0247819 A1    Sep. 3, 2015

Related U.S. Application Data

(60) Provisional application No. 61/579,365, filed on Dec. 22, 2011.

(51) Int. Cl.
*C12Q 1/00* (2006.01)
*C12Q 1/04* (2006.01)
(Continued)

(52) U.S. Cl.
CPC ........ *G01N 27/4145* (2013.01); *B01L 3/5021* (2013.01); *C12Q 1/04* (2013.01);
(Continued)

(58) Field of Classification Search
None
See application file for complete search history.

(56) References Cited

U.S. PATENT DOCUMENTS

| 4,250,266 A | 2/1981 | Wade |
| 5,578,269 A | 11/1996 | Yaremko et al. |

(Continued)

FOREIGN PATENT DOCUMENTS

| CN | 102131914 A | 7/2011 |
| CN | 102203597 A | 9/2011 |

(Continued)

OTHER PUBLICATIONS

Bettaieb et al., (Bioelectrochemistry. 2007. vol. 71(2):118-25).*
(Continued)

*Primary Examiner* — Ja'Na Hines
(74) *Attorney, Agent, or Firm* — Botos Churchill IP Law LLP (57) ABSTRACT

An array of micro-chambers (220) with individual ion sensitive field effect transistors (ISFETs) (300) disposed therein for monitoring single cell activity in the microarray to determine the presence or absence of microorganisms in a sample (390). In addition to the presence or absence of a single cell, certain further embodiments contemplate monitoring cell behavior. Cell behavior includes the entire range of cell activity as well as cell response to changes in environmental conditions of changes in response due to the addition of sample constituents.

15 Claims, 4 Drawing Sheets

(51) Int. Cl.
  *C12Q 1/06* (2006.01)
  *C12N 13/00* (2006.01)
  *G01N 27/414* (2006.01)
  *B01L 3/00* (2006.01)
  *G01N 33/487* (2006.01)

(52) U.S. Cl.
  CPC .............................. *G01N 33/48735* (2013.01); *B01L 2300/0636* (2013.01); *B01L 2300/0851* (2013.01); *B01L 2300/0893* (2013.01); *B01L 2400/043* (2013.01); *B01L 2400/0409* (2013.01); *B01L 2400/0415* (2013.01); *G01N 2800/26* (2013.01)

(56) References Cited

U.S. PATENT DOCUMENTS

| | | | |
|---|---|---|---|
| 5,705,384 | A | 1/1998 | Berndt |
| 5,795,773 | A | 8/1998 | Read et al. |
| 6,086,824 | A | 7/2000 | Fanning et al. |
| 6,750,064 | B2 | 6/2004 | Stahly et al. |
| 7,948,015 | B2 | 5/2011 | Rothberg et al. |
| 2004/0005572 | A1 | 1/2004 | Rosner et al. |
| 2004/0197771 | A1 | 10/2004 | Powers et al. |
| 2005/0064469 | A1 | 3/2005 | Schulz et al. |
| 2006/0281094 | A1 | 12/2006 | Squirrell et al. |
| 2007/0111225 | A1 | 5/2007 | Lambert et al. |
| 2008/0072664 | A1 | 3/2008 | Hansen et al. |
| 2008/0318243 | A1 | 12/2008 | Haga et al. |
| 2009/0026082 | A1* | 1/2009 | Rothberg ............. C12Q 1/6869 204/556 |
| 2009/0127589 | A1* | 5/2009 | Rothberg ............. C12Q 1/6874 257/253 |
| 2010/0300895 | A1 | 12/2010 | Nobile et al. |
| 2011/0151503 | A1 | 6/2011 | Galiano |
| 2014/0141408 | A1 | 5/2014 | Gulak et al. |
| 2015/0167044 | A1 | 6/2015 | Berndt |

FOREIGN PATENT DOCUMENTS

| | | |
|---|---|---|
| EP | 2430461 A2 | 3/2012 |
| JP | 10313892 | 12/1998 |
| JP | 2003083932 A | 3/2003 |
| JP | 2006345832 A | 12/2006 |
| JP | 2009002808 A | 1/2009 |
| JP | 2011512158 A | 4/2011 |
| JP | 2012506557 A | 3/2012 |
| WO | 9639533 A1 | 12/1996 |
| WO | 2009035647 A1 | 3/2009 |
| WO | 2009158006 A2 | 12/2009 |
| WO | 2010118235 A1 | 10/2010 |
| WO | 2014039082 A1 | 3/2014 |
| WO | 2014080292 A2 | 5/2014 |

OTHER PUBLICATIONS

J.C Van Kerkhof et al: "The ISFET based heparin sensor with a monolayer of protamine as affinity ligand", Biosensors and Bioelectronics, Jan. 1, 1995 (Jan. 1, 1995), pp. 269-282, XP055200348, England DOI: 10.1016/0956-5663(95)96846-Q Retrieved from the Internet: URL:http://www.sciencedirect.com/science/article/pii/095656639596846Q * p. 274, col. 1, paragraph 2 *.
Supplementary European Search Report for Application No. EP12860579 dated Jul. 22, 2015.
Bettaieb, F. et al., "Immobilization of *E. coli* bacteria in three-dimensional matrices for ISFET biosensor design," Bioelectrochemistry 71 pp. 118-125 (2007).
Cambiaso, A, et al., "An H+ -FET-based system for on-line detection of microorganisms in waters," Sensors and Actuators B 34 pp. 245-251 (1996).
Castellarnau, M. et al., "Integrated cell positioning and cell-based ISFET biosensors," Sensors and Actuators B 120, pp. 615-620 (2007).
Ges, I. et al., "On-chip acidification rate measurements from single cardiac cells confined in sub-nanoliter volumes," Biomed. Microdevices 10 pp. 347-354 (2008).
Gotoh, M., "Construction of Amorphous Silicon ISFET," Sensors and Actuators, vol. 16, pp. 55-65 (1989).
Pourciel-Gouzy M. L., et al., "Development of pH-ISFET sensors for the detection of bacterial activity," Sensor and Actuators B 103 pp. 247-251 (2004).
International Search Report for Application No. PCT/US2012/070538 dated Apr. 16, 2013.
Chinese Search Report within Chinese Office Action dated Sep. 1, 2016 for Chinese Application No. 201280069701.X.
G. Funke et al., Use of the BD Phoenix Automated Microbiology System for Direct Identification and Susceptibility Testing of Gram-Negative Rods from Positive Blood Cultures in a Three-Phase Trial; Journal of Clinical Microbiology, vol. 42, No. 4, pp. 1466-1470, published Apr. 2004.
C. Estes et al., "Reagentless detection of microorganisms by intrinsic fluorescence", Biosensors and Bioelectronics vol. 18 (2003), pp. 511-519; published May 2003.
Carbonnelle et al. (2007) Rapid identification of Staphylococci isolated in clinical microbiology laboratories by matrix-assisted laser desorption ionization-time of flight mass spectrometry. J Clin Microbiol 45 2156-61.
Anhalt J, Fenselau C (1975) Identification of bacteria using mass spectrometry. Anal Chem 47219-25.
Degand et al. (2008) Matrix-assisted laser desorption ionization-time of flight mass spectrometry for identification of nonfermenting gram negative bacilli isolated from cystic fibrosis patients. J Clin Microbiol 46: 3361-7.
General information on SST tubes from Becton Dickinson website (2010).
Isenberg et al. Prototype of a Fully Automated Device for Determination of Bacterial Antibiotic Susceptibility in the clinical Laboratory; Applied Microbiology, vol. 22, No. 6, pp. 980-986, published Dec. 1971.
Wm. M. Dunne, Jr., et al., In-house validation of the BACTEC 9240 blood culture system for detection of bacterial contamination in platelet concentrates; Transfusion, vol. 45, pp. 1138-1142, published Jul. 2005.
M.J. Bruins et al. Identification and Susceptibility Testing of Enterobacteriaceae and Pseudomonas aeruginosa by Direct Inoculation from Positive BACTEC Blood Culture Bottles into Vitek 2; Journal of Clinical Microbiology, vol. 42, No. 1, pp. 7-11, published Jan. 2004.
G. M. Trenholme et al., Clinical Impact of Rapid Identification and Susceptibility Testing of Bacterial Blood Culture Isolates; Journal of Clinical Microbiology, vol. 27, No. 6, pp. 1342-1345; published Jun. 1989.
M. S. Ammor; Recent Advances in the Use of Intrinsic Fluorescence for Bacterial Identification and Characterization; Journal of Fluorescence, vol. 17, pp. 455-459; published Jul. 12, 2007.
Q. Zhu et al., Raman Spectroscopic Measurement of Relative Concentrations in Mixtures of Oral Bacteria; Applied Spectroscopy, vol. 61, No. 11, pp. 1233-1237; published Nov. 2007.
L. Leblanc et al. Monitoring the identity of bacteria using their intrinsic fluorescence; FEMS Microbiology Letters, vol. 211, pp. 147-153: published Apr. 17, 2002.
K. Gopinath et al., Novel Method for Clearing Red Blood Cell Debris From BacT/ALERT Blood Culture Medium for Improved Microscopic and Antimycobacterial Drug Susceptibility Test Results; Journal of Clinical Laboratory Analysis, vol. 21, pp. 220-226, published 2007.

\* cited by examiner

METHODS AND APPARATUS FOR RAPID DETECTION OF INFECTIOUS MICROORGANISMS

CROSS-REFERENCE TO RELATED APPLICATIONS

The present application claims the benefit of the filing date of U.S. Provisional Application No. 61/579,365, filed Dec. 22, 2011, entitled Methods and Apparatus for Rapid Detection of Infectious Microorganisms, the disclosure of which is hereby incorporated herein by reference.

BACKGROUND OF THE INVENTION

Sepsis is a significant healthcare issue due to its high frequency of occurrence and high mortality rate in hospitals. Sepsis is characterized by a whole-body inflammatory state, called a systemic inflammatory response syndrome (SIRS), and by the presence of a known or suspected infection. The immune system may cause this inflammatory response as a consequence of microbes in the blood, urine, lungs, skin, or other tissues, for example. One of the leading causes of sepsis is a bloodstream infection (BSI). BSI is most commonly diagnosed by a blood culture, in which a sample of blood is incubated with a medium in an atmosphere controlled to promote bacterial growth. Current automated blood culture systems can take 12-48 hours to detect the presence of infectious microorganisms in blood and can take up to 5 days to rule out the presence of any infectious microorganisms. It can take up to another 12-48 hours to identify the infectious microorganisms by sub-culturing the positive blood culture and performing identification and antimicrobial susceptibility tests. These results can be too late to alter the treatment course and result in the death of the patient. It would be advantageous if the time it takes to detect the presence of infectious microorganisms in the blood or other body fluid or tissue could be shortened to less than 24 hours, and more preferentially to less than 8 hours. Consequently, more time effective methods and apparatus for detecting the presence or absence of infectious microorganisms in a biological sample to determine, for example, if a patient has a BSI continue to be sought.

BRIEF SUMMARY OF THE INVENTION

Described herein are methods and apparatus for rapid detection of microorganism growth in biological samples (e.g. blood) for analysis to determine the presence or absence of infectious microorganisms in the samples. In one embodiment, arrays of miniaturized chambers with individual ion sensitive field effect transistors (ISFET), which, for example, may be located at the base of the chambers, are used to determine the presence or absence of even a single microorganism in the sample. In addition to the presence or absence of a single cell, certain further embodiments contemplate monitoring cell behavior. Cell behaviors include the entire range of cell activity (respiration, growth, cell division, etc.) as well as cell response to changes in environmental conditions (e.g. temperature, pH) or changes in response due to the addition of sample constituents (e.g. antibiotics, antifungals, nutrients, etc.). Cell behaviors can be monitored using a variety of known techniques. For example, organism growth curves are generated and data regarding cell response is obtained. Such curves can chart cell growth over time or values of a sample condition (e.g. $CO_2$ concentration) over time. As such data is being gathered (typically in real time) the change in growth rate or cell metabolic activity due to the addition of sample constituent (e.g. an antibiotic) can also be observed. Methods and apparatus disclosed herein may be used for, inter alia, microorganism detection, microorganism identification, and assessment of response of microorganisms to either changes in environmental conditions or sample constituents (e.g. antimicrobial agents, such as antibiotics).

The miniaturized chamber on the top of an individual ISFET has a volume ranging from 1 femtoliter to 1 microliter, preferably from 1 picoliter to 1 nanoliter. The volume of the chamber is selected to ensure that the volume of the contents is sufficiently low to enable the detection of even small changes in sample environment (e.g. pH) due to the presence of even a single microorganism in the chamber. The shape of the chamber and the shape of the opening in the chamber is largely a matter of design choice. Conventional shapes such as rectangular, cubic, or cylindrical are contemplated. The wall of the chamber can be vertical, tilted, or any other shape or form. In certain embodiments, design choice will dictate, whether, and to what degree, a chamber wall will be tapered. The degree of taper can affect the ability of the chamber to retain the single cell within the chamber. The depth of the wells, for example from about 5 μm to about 100 μm, can also be selected based upon objectives. For example, and not by way of limitation, the depth of the chamber can localize or concentrate the source of the signals being monitored. For example, in embodiments where the chamber with a relatively small volume is disposed beneath a much larger volume for holding the bulk of the sample (described in detail below) a certain verticality will require it to take longer for changes in the chamber environment (e.g. a pH change caused by protons that result from cell metabolic activity) to diffuse away from the sensor and out of the chamber, giving more time for the change to be detected. In further examples, the size the chamber size may be optimized to accommodate one, two, or even more than two microorganisms within the chamber, increasing the sensitivity of detection and shortening the time to detection. The size of the chamber may also be selected to receive microorganisms while simultaneously preventing larger mammalian cells from entering the chamber. Therefore, chamber design can provide selectivity in the type of cell being sensed.

In one embodiment, the apparatus is comprised of an array with 5,000 to 10,000 chambers. The array may include as few as 100 chambers or less, or as many as 10,000,000 chambers or more. The size of the array is largely a matter of design choice. While exemplary array sizes are described herein, the embodiments described herein can be readily adapted to other array sizes. The array can be of single or multi-row arrangement. As noted above, each chamber in the array includes an individual ISFET, which may, for example, be disposed at the bottom of the chamber. Although the embodiment described herein describes the ISFET as disposed in the bottom of the chamber, ISFET placement within the chamber is not restricted. ISFET placement within the chamber is a matter of design choice. In another embodiment, the apparatus is comprised of a two-dimensional array with up to 10,000 rows and 10,000 columns of chambers, each with an individual ISFET, for example built underneath the chamber, preferably with fewer than 500 rows and 500 columns of chambers.

In one embodiment the array is placed in and contained by a housing that can also receive samples, either before or after testing, or both. The housing may provide, for example, a physical structure that holds a large sample volume and allows microorganisms within the sample to be driven into the wells of the array without the need to manually transfer sample to each well individually. Again, the housing configuration will largely be a matter of design choice, based on the size and configuration of the array, the mechanisms used to drive the organisms into the underlying chamber, etc. For example, the housing may additionally or alternatively include electronics that generate an electrostatic field that can drive microorganisms to the chambers. The housing may also include components that generate a magnetic field. The magnetic field is used to direct microorganisms into the chambers by binding or otherwise coupling microorganisms to magnetic or paramagnetic particles.

In one example, the housing includes a first end adapted to receive a sample and a volume for receiving the sample therein. The array of chambers is disposed in the volume such that sample in the housing is above the array of chambers. Each chamber is in fluid communication with the overlying housing volume and has an ISFET disposed therein, the ISFET being configured to detect a change in the sample indicative of at least one of the presence or absence or response of a microorganism in the sample.

It is noted that, in certain applications, due to the arrangement of the components and the concentration of microorganisms in the sample, it is expected that microorganisms will often only end up in a fraction of the chambers. The "empty" chambers can then be used as a control to subtract out background signals from those chambers being monitored for changes in condition to microorganism activity in the chamber.

The substrate used for ISFET fabrication can be made of silicon, glass, ceramic or plastic materials. ISFETs are well known to one skilled in the art and are not described in detail herein. ISFETS and the manufacture of ISFETS are described in WO2010/118235 entitled "DNA Cell Conjugates" to Hsiao, et al., U.S. Pat. No. 7,948,015 entitled "Methods and Apparatus for Measuring Analytes Using Large Scale FET Arrays" to Rothberg et al., and Gotoh, M., "Construction of Amorphous Silicon ISFET," *Sensors and Actuators*, Vol. 16, pp. 55-65 (1989), which are incorporated by reference herein. Typically, ISFETs are built on n- or p-type silicon semiconductor materials. An embodiment of the ISFET apparatus disclosed herein can also be built economically on glass substrate, much like the active matrix thin-film-transistors (TFTs) used in driving modern liquid crystal displays. It is also conceivable to build the ISFET on a ceramic or plastic substrate.

In general, the proposed methods include the fabrication of an array of miniaturized chambers with individual ISFETs integrated with the chamber, the integrated chambers/ISFETS, for example, being disposed on a supporting substrate. The method also includes placing the miniaturized chambers in fluid communication with a system that will allow microorganisms to enter into individual chambers. As described above, chambers may be designed to accommodate a single microorganism, or two or more microorganisms. Mechanisms for "driving" the microorganisms in the sample (if present) include, for example, centrifugation. Other driving mechanisms are contemplated herein, such as by electrostatic and/or magnetic forces as previously described, or by sonic forces, affinity, or gravitational forces. The selected mechanism will successfully drive the microorganisms into the chamber but not adversely affect the viability of the microorganisms. The method further contemplates the addition of growth media to the sample to create conditions for microorganism growth. The small amount of volume allows the ISFET to detect even small changes in pH or other sample conditions indicative of the presence and/or response of microorganisms in the chamber.

For example, different microorganisms respond differently and identifiably to different media, antibiotics and/or unique substrates (i.e. nutrients identified by enzymes that are specific to certain microorganisms). Therefore, monitoring the conditions in the chamber for changes indicative of microorganism metabolic activity in response to a particular additive can yield information on microorganism identity in addition to an indication that a viable microorganism is present. For example, changes in the sample in one chamber with antimicrobials may be compared to changes in the sample in another chamber without antimicrobials to determine the susceptibility of microorganisms within the chambers to the antimicrobial. Additionally, based on how an unknown microorganism metabolically responds to known compounds, an unknown microorganism in a sample may be identified. An embodiment of the invention further contemplates the addition to the sample of compounds that amplify signal detection. For example, the metabolism of certain sugars produces a relatively large amount of acid and/or carbon dioxide, the production of which in turn creates a commensurately larger signal for detection by the ISFET. Such sugars, referred to here as "inducer substrates," induce a certain response in the microorganism that enhances/facilitates detection or measurement.

As stated above, a variety of mechanisms can be used to drive the microorganisms into the chamber. The methods to position microorganisms into the individual chambers on top of the ISFETs include centrifugation, direct electrical field and electrophoresis. Alternatively, solid objects, such as latex beads or magnetic beads, which are smaller than the size of the chambers on top of the ISFETs, can be functionalized with microorganism-binding ligands. Then, samples containing microorganisms are mixed with the functionalized beads, and the microorganisms bind with the ligands on the beads. The beads with microorganisms bound thereto are then driven into the chambers on top of the ISFETs by gravity or external forces, such as centrifugation or magnetic fields. The ligands attached to the beads can be selected from nonspecific microorganism-binding agents known to those skilled in the art, such as apolipoprotein H, fibronectin, lectin, and mannose binding lectin. The ligands attached to the beads can also be a combination of different specific microorganism-binding agents such as pan-gram-positive antibody, pan-gram-negative antibody, pan-yeast antibody and pathogen-specific antibodies.

DETAILED DESCRIPTION

Arrays of miniaturized chambers with individual ion sensitive field effect transistors (ISFET) are used to determine the presence or absence of even a single microorganism in the sample. The ISFETS are positioned in chambers adapted to receive sample that may contain on or more microorganisms. The ISFET is positioned in the chamber. In certain embodiments, the ISFET is positioned at the bottom of the chamber. In one embodiment, the apparatus is comprised of an array with 5,000 to 10,000 chambers. The array may include as few as 100 chambers or less, or as many as 10,000,000 chambers or more. The array can be of single or multi-row arrangement. As noted above, each chamber in the array includes an individual ISFET, for example, disposed at the bottom of the chamber. In another embodiment, the apparatus is comprised of a two-dimensional array with up to 10,000 rows and 10,000 columns of chambers, each with an individual ISFET, for example built underneath the chambers, preferably with fewer than 500 rows and 500 columns of chambers. In one embodiment the array is placed in and contained by a housing that can also accommodate samples, either before or after testing, or both. The housing may provide, for example, a physical structure that holds a large sample volume and allows organisms within the sample to be driven into the wells of the array without the need to manually transfer sample to each well individually. As described above, the housing may include additional or alternative components, such as electronics or magnets to provide an electrostatic or magnetic field to the volume of the housing as well as to the array of chambers in the housing. The electrostatic or magnetic field can be used to drive microorganisms into the chambers. Again, the housing configuration will largely be a matter of design choice, based on the size and configuration of the array, the mechanisms used to drive the organisms into the underlying chamber, etc. It is noted that, in certain applications, because of the contemplated arrangements, it is likely that microorganisms will only end up in a fraction of the chambers.

The miniaturized chamber on the top of an individual ISFET has a volume ranging from 1 femtoliter to 1 microliter, preferably from 1 picoliter to 1 nanoliter. The volume of the chamber is selected to ensure that the volume of the contents is sufficiently low to enable the detection of even small changes in sample environment (e.g. pH) due to the presence of even a single microorganism in the chamber. The shape of the chamber and the shape of the opening in the chamber is largely a matter of design choice. Conventional shapes such as rectangular, cubic, or cylindrical are contemplated. The wall of the chamber can be vertical, tilted, or any other shape or form. In certain embodiments, design choice will dictate, whether, and to what degree, a chamber wall will be tapered. The degree of taper can affect the ability of the chamber to retain the single cell within the chamber. The depth of the wells, for example from about 5 µm to about 100 µm, can also be selected based upon objectives. For example, and not by way of limitation, the depth of the chamber can localize or concentrate the source of the signals being monitored. For example, in embodiments where the chamber with a relatively small volume is disposed beneath a much larger volume for holding the bulk of the sample (described in detail below) a certain verticality will require it to take longer for changes in the chamber environment (e.g. a pH change caused by protons that result from cell metabolic activity) to diffuse away from the sensor and out of the chamber, giving more time for the change to be detected. In further examples, the size the chamber size may be optimized to accommodate one, two, or more microorganisms within the chamber. Controlling the number of microorganisms can increase the sensitivity of detection and shorten the time to detection. The size of the chamber may also be selected to allow the chambers to receive microorganisms while simultaneously preventing larger mammalian cells from entering the chamber. This provides an amount of selectivity in the type of cell being detected. By way of example, and not limitation, a chamber may have an opening on the order of about 5 µm, which size may act as a filter to prevent mammalian cells (which may be on the order of about 10 µm), from entering the chamber while allowing bacterial cells to enter the chamber.

It is believed that the concentration of infectious microorganisms in a sample (e.g. blood) can be as low as one in ten milliliters (mL) at the time that the sample is drawn from a patient. Such low concentrations are below the current limits for reliable determination of the presence or absence of the microorganisms in the sample. Therefore, known methods for detection require growing the number of microorganisms to a number/concentration capable of reliable detection or increasing the sensitivity of the sensor used. Other known methods of detection use a molecular approach that also has its drawbacks. Molecular detection using nucleotide primers and probes is generally known in the art. The primers and probes hybridize to the DNA or RNA of one or more target organisms. In such molecular approaches, the organisms (or the cells of multi-cell organisms) generally must be destroyed to obtain the nucleic acid to be amplified and detected. Since the amount of nucleic acid so obtained is often not enough to obtain a detectable signal, amplification steps are required (which steps are performed in conjunction with the primers and other amplification reagents such as polymerase enzyme). Because such assays are target specific, there must be at least some idea of the identity of the target organism in order to design a primer/probe set for the detection of the target. Additionally, molecular assays cannot currently distinguish between DNA derived from live and dead organisms. This drawback in current molecular methods requires either the addition of sample preparation steps that remove nucleic acids from the specimen not originating from the living target organism (e.g. circulating pathogen DNA), or a possibly incorrect assumption must be made that the nucleic acid that is detected represents a current infection. Therefore such assays are complicated to design, complicated to perform, and lack accuracy. Therefore, assays which are not target specific, but can yield information about the target, are very desirable because they are capable of wide deployment.

Figure 1:
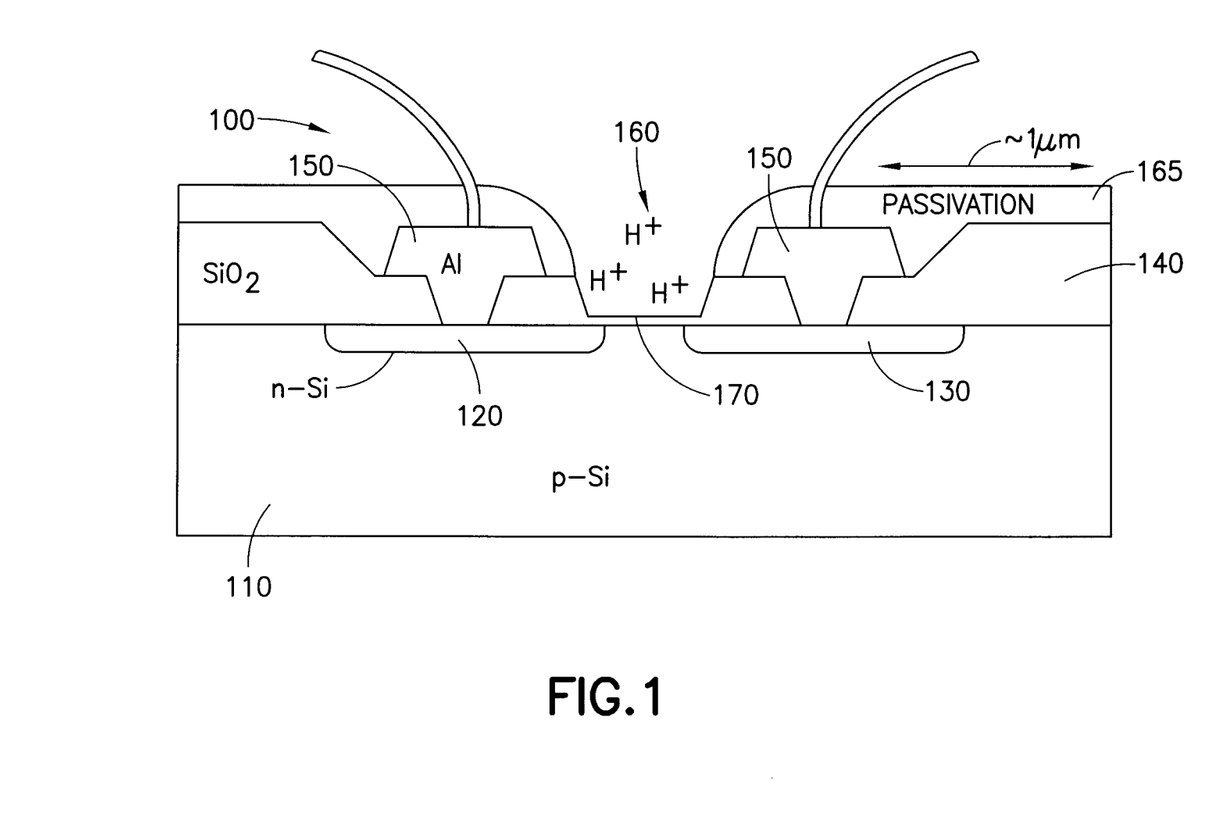
FIG. 1 is a schematic of an ISFET that is used in conjunction with the method and apparatus for BSI detection described herein.

As noted above, ISFETs are used to measure ion concentrations or changes in ion concentrations or concentration ratios in solution. When the ion concentration (such as H+) changes, the current through the transistor will change accordingly. Referring to FIG. 1, in such an arrangement, the solution 160 is used as the gate electrode. A voltage between the substrate 110 and gate dielectric (e.g. an oxide) surfaces 170 arises due to an ion sheath. The surface hydrolysis of Si—OH groups of the gate materials 160/170 varies in aqueous solutions due to the pH value of the solution. Typical gate dielectric materials 170 include $SiO_2$, $Si_3N_4$, $Al_2O_3$ and $Ta_2O_5$. The ISFET 100 also has source and drain electrodes 150 in contact with doped silicon source and drain regions 120 and 130, respectively. An insulator 140 is formed over the ISFET, with contact windows through the insulator for the source and drain electrodes 150. A passivation layer 165 is formed over the device to ensure device integrity over time.

ISFETs have been used previously for microorganism detection in water or food production. Cambiaso, A., et al., "An $H^+$-FET-based system for on-line detection of microorganisms in waters," *Sensors and Actuators B* 34 pp.

245-251 (1996) demonstrates a flow-through system with a $Si_3N_4$ ISFET for on-line detection of *E. coli* in water. Pourciel-Gouzy M. L., et al., "Development of pH-ISFET sensors for the detection of bacterial activity," *Sensor and Actuators B* 103 pp. 247-251 (2004) demonstrates the concept of adaptation of pH-ISFET sensors for the detection of *Lactobactillus acidophilus* activity using Plexiglas or PDMS microtanks. Castellarnau, M. et al., "Integrated cell positioning and cell-based ISFET biosensors," *Sensors and Actuators B* 120, pp. 615-620 (2007) demonstrates a cell-based biosensor comprised of integrated dielectrophoretic (DEP) electrodes for cell positioning and ISFETs. Castellarnau et al. further demonstrates that when *E. coli* is positioned on the ISFET gate by local DEP, the local pH was lowered within minutes after the addition of sugar. In contrast, pH values obtained either with the reference ISFET or the commercial pH-meter in bulk solution were minimal. Bettaieb, F. et al., "Immobilization of *E. coli* bacteria in three-dimensional matrices for ISFET biosensor design," *Bioelectrochemistry* 71 pp. 118-125 (2007) describes an electrochemical system based on a microbial biosensor using an *E. coli* K-12 derivative as a primary transducer to detect biologically active agents. An ISFET sensor was used to measure the pH changes of bacteria immobilized in agarose gels. With regard to measurement of single cell activity using pH electrodes, Ges, I. et al., "On-chip acidification rate measurements from single cardiac cells confined in sub-nanoliter volumes," *Biomed. Microdevices* 10 pp. 347-354 (2008) describes a microfluidic system to trap and measure acidification rates of single cardiac myocytes. In the device described by Ges et al., a concentrated solution of mycotyes is flowed through a channel in a clear PDMS microfluidic device with integrated iridium oxide electrode sensors using positive pressure. Once the cells pass over the sensor, as confirmed with visual inspection, negative pressure is applied to stop the main solution flow, and mechanical valves are sealed on each side of the sensor to stop residual flow and to trap a single cell at the sensor location to allow for pH measurements. Therefore, the references described above all require complicated capture strategies for capturing single cell microorganisms, and are limited in the amount of information that they can glean from the captured microorganisms. All of the references described herein are incorporated by reference.

As noted above, a discrete ISFET has been used for the detection of large amounts of microorganisms (or the changes in a sample as the result of a large number of microorganisms) in the sample, with microorganism concentrations often on the order of $10^8$ cfu/ml in bulk (milliliters) sample solution. Embodiments of the invention described herein require fewer microorganisms in complex clinical specimens such as blood, sputum, saliva, cerebrospinal fluid, pleural fluid, peritoneal fluid and urine to accomplish detection. Embodiments of the invention described herein further enable detection and kinetic measurement of microorganism response due to perturbations in the sample or sample conditions or that result from the application of pre-defined conditions.

ISFET technology on a smaller scale has been used for detecting and analyzing cell constituents, more particularly for DNA sequencing. U.S. Pat. No. 7,948,015 to Rothberg et al., also incorporated by reference herein, describes a large scale FET array that monitors changes in hydrogen ion concentration to sequence DNA. Target DNA is bound to small beads, which facilitate the placement of the DNA into the microwells of the array, and different nucleotide bases are sequentially flowed over the beads with DNA. Binding events are noted based on changes in pH at the ISFET, helping the user determine the sequence of the target DNA.

Figure 2A:
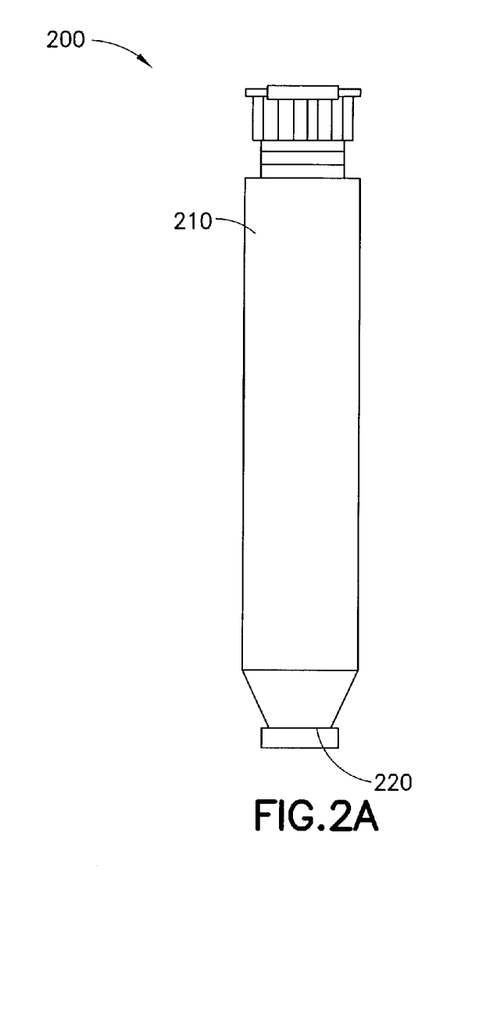
FIG. 2A is a side view of a sample collection vessel with an array of miniaturized ISFET-containing chambers disposed at the bottom thereof.
Figure 2B:
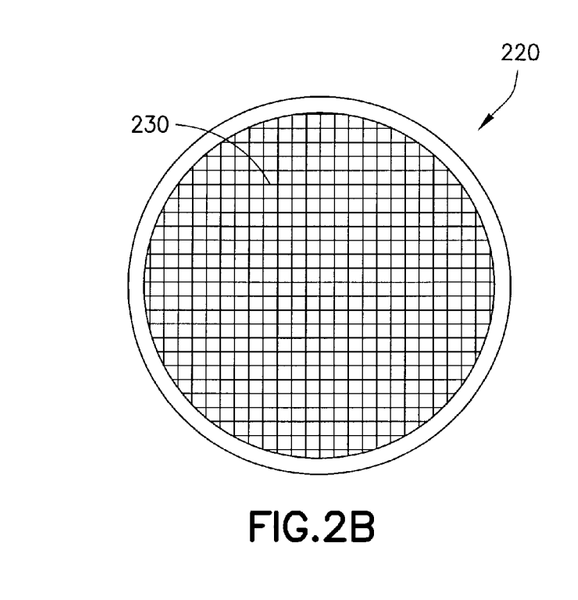
FIG. 2B is a bottom view of the array of miniaturized ISFET-containing chambers of FIG. 2A.

Referring to FIGS. 2A-B, in one embodiment, a sample collection tube 200 is provided. In one embodiment, the sample tube is an evacuated, sterilized centrifugable collection tube 210 such as a BD Vacutainer® tube from Becton Dickinson and Company. An array of microchambers 220 is disposed proximate the bottom of the tube 210. In this illustrated embodiment, an ISFET 230 is disposed at the bottom of each microchamber.

According to one embodiment, blood is drawn from a patient into the tube 210 with organism-stabilizing and blood-lysis reagents contained therein. In other embodiments, the sample is drawn or otherwise obtained (such as in the case of swabs for patient or environmental samples) and undergoes preparation or sample processing (e.g. separation from other sample constituents) before being added to the tube 210. As noted above, in this particular embodiment, the tube 210 has an array of micron-size chambers 220, each micron-size chamber with an ISFET 230 at the chamber base. The micro-chamber array is supported by a substrate.

In one exemplary configuration, in order to drive any microorganisms in the tube down into the micro-chambers, the tube is subjected to a vortex and spin, for example, at a relative centrifugal force (RCF) of up to about 12 kg for up to 30 minutes to complete the lysis of human cells in the sample, and to drive microorganisms in the sample down into individual ones of the micron size chambers at the base of the tube. As known to one skilled in the art, a density gradient gel can be used to separate human cellular debris in the sample from microorganisms in the sample. The lysed human cellular debris will remain in the supernatant, which is discarded. In order to facilitate microorganism metabolism and growth (e.g. cell division and other metabolic activity capable of detection by an ISFET), growth media, for example BD BACTEC™ Plus Aerobic medium by Becton, Dickinson and Company, is added to the portions of the sample remaining in the micron sized chambers. The ISFET will provide a signal if the sample pH changes, and that change in pH will be equated with the presence of a microorganism in the micro-chamber.

The conditions of the sample may be optimized to recover microorganisms from the specimen matrix. For example, when a patient has been pretreated with antimicrobials, a matrix or medium is required to separate the antimicrobial from the microorganisms. The sample environment may also be controlled to facilitate detection. For example, the sample can be combined with components that increase proton generation by microorganisms in the sample. The sample can be combined with additives and subjected to conditions that drive the selective growth of certain organisms over others. For example, when samples contain non-pathogenic background microorganisms, conditions and nutrients are selected to favor growth of the target microorganism over the background microorganisms. In one embodiment of the invention, there will be a small number of wells occupied by microorganisms relative to the total number of wells due to the expected small concentration of microorganisms in a sample. The empty wells can be used as negative controls to account for, and subtract out, background signals from material such as cellular debris, allowing for greater sensitivity in the detection of pH change in the occupied wells.

Figure 3:
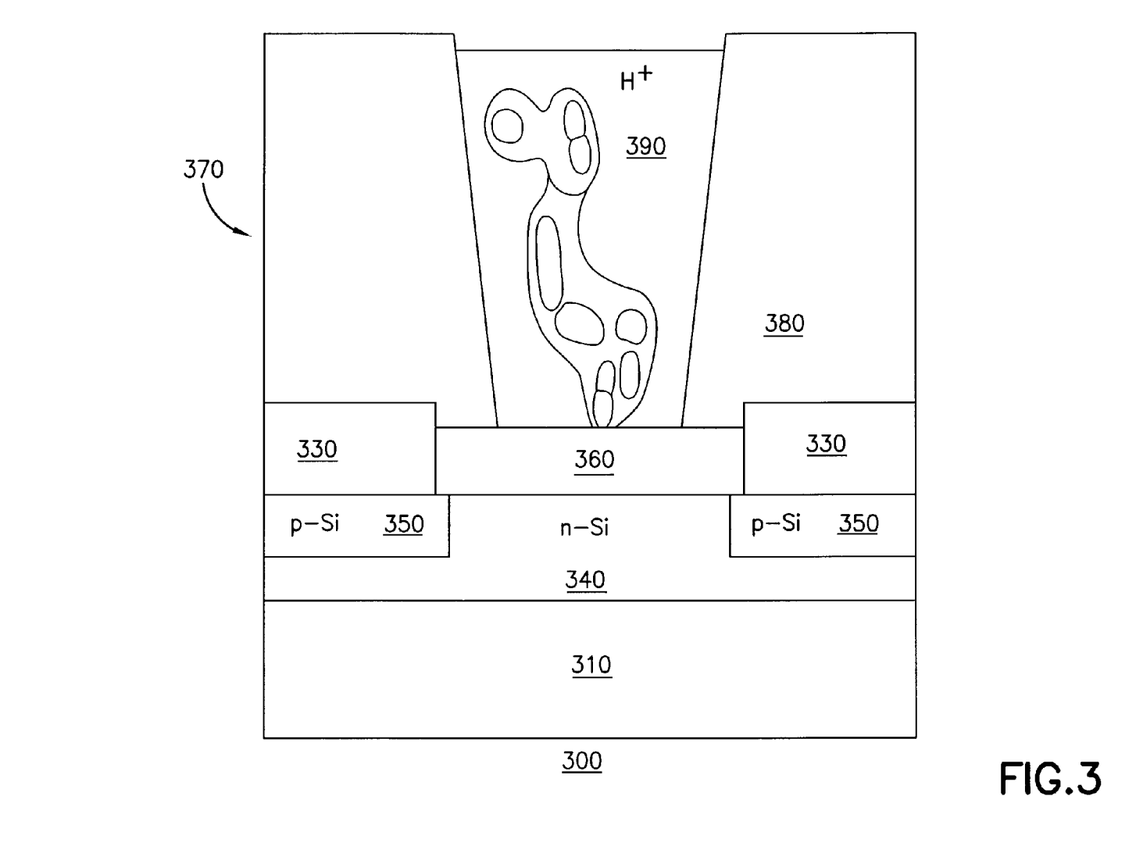
FIG. 3 is a schematic cross section of an individual miniaturized chamber disposed on an ISFET.
Figure 4:
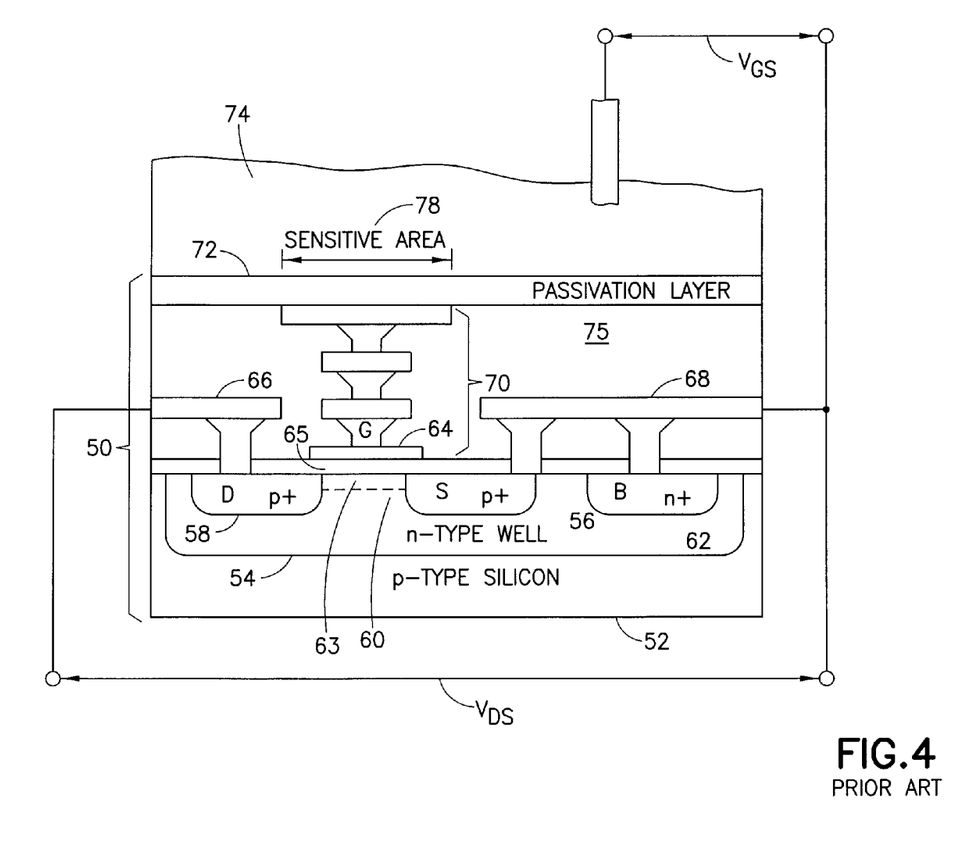
FIG. 4 is a schematic cross section of another p-type ion-sensitive field effect transistor from the prior art.

This is explained with reference to FIGS. 3-4. FIG. 3 illustrates an ISFET 300. The ISFET is formed on a glass substrate 310. A semiconductor layer (e.g. silicon) 340 is formed on the substrate 310 with source 350 and drain 350 regions formed therein. Source electrode 320 and drain electrode 330 are formed on the source and drains regions 350. On the silicon layer 340 is formed a layer of metal oxide 360. Examples of metal oxide include aluminum oxide ($Al_2O_3$), tantalum pentoxide ($Ta_2O_5$) and silicon dioxide ($SiO_2$). FIG. 4 illustrates an alternate embodiment of an ISFET and is more fully described in Rothberg et al., U.S. Pat. No. 7,948,015.

FIG. 4 illustrates a cross-section of a p-type (p-channel) ISFET 50 fabricated using a conventional CMOS (Complimentary Metal Oxide Semiconductor) process. P-type ISFET fabrication is based on a p-type silicon substrate 52, in which an n-type well 54 forming a transistor "body" is formed. Highly doped p-type (p+) regions S and D, constituting a source 56 and a drain 58 of the ISFET, are formed within the n-type well 54. A highly doped n-type (n+) region B is also formed within the n-type well to provide a conductive body (or "bulk") connection 62 to the n-type well. An oxide layer 65 is disposed above the source, drain and body connection regions, through which openings are made to provide electrical connections (via electrical conductors) to these regions; for example, metal contact 66 serves as a conductor to provide an electrical connection to the drain 58, and metal contact 68 serves as a conductor to provide a common connection to the source 56 and n-type well 54, via the highly conductive body connection 62. A polysilicon gate is formed above the oxide layer at a location above a region 60 of the n-type well 54, between the source 56 and the drain 58. Because it is disposed between the polysilicon gate 64 and the transistor body (i.e., the n-type well), the oxide layer 65 often is referred to as the "gate oxide."

Like a MOSFET, the operation of an ISFET is based on the modulation of charge concentration caused by a MOS (Metal-Oxide-Semiconductor) capacitance constituted by the polysilicon gate 64, the gate oxide 65 and the region 60 of the n-type well 54 between the source and the drain. When a negative voltage is applied across the gate and source regions ($V_{GS}$<0 Volts), a "p-channel" 63 is created at the interface of the region 60 and the gate oxide 65 by depleting this area of electrons. This p-channel 63 extends between the source and the drain, and electric current is conducted through the p-channel when the gate-source potential $V_{GS}$ is negative enough to attract holes from the source into the channel. The gate-source potential at which the channel 63 begins to conduct current is referred to as the transistor's threshold voltage $V_{TE}$ (the transistor conducts when $V_{GS}$ has an absolute value greater than the threshold voltage $V_{TH}$). The source is so named because it is the source of the charge carriers (holes for a p-channel) that flow through the channel 63; similarly, the drain is where the charge carriers leave the channel 63.

In the ISFET 50 of FIG. 4, the n-type well 54 (transistor body), via the body connection 62, is forced to be biased at a same potential as the source 56 (i.e., $V_{SB}$=0 Volts), as seen by the metal contact 68 connected to both the source 56 and the body connection 62. This connection prevents forward biasing of the p+ source region and the n-type well, and thereby facilitates confinement of charge carriers to the area of the region 60 in which the channel 63 may be formed. Any potential difference between the source 56 and the body/n-type well 54 (a non-zero source-to-body voltage $V_{SB}$) affects the threshold voltage $V_{TH}$ of the ISFET according to a nonlinear relationship, and is commonly referred to as the "body effect," which in many applications is undesirable.

As also shown in FIG. 4, the polysilicon gate 64 of the ISFET 50 is coupled to multiple metal layers disposed within one or more additional oxide layers 75 disposed above the gate oxide 65 to form a "floating gate" structure 70. The floating gate structure is so named because it is electrically isolated from other conductors associated with the ISFET; namely, it is sandwiched between the gate oxide 65 and a passivation layer 72. In the ISFET 50, the passivation layer 72 constitutes an ion-sensitive membrane that gives rise to the ion-sensitivity of the device; i.e., the presence of ions in an "analyte solution" 74 (a solution containing ions of interest) in contact with the passivation layer 72, particularly in a sensitive area 78 above the floating gate structure 70, alters the electrical characteristics of the ISFET so as to modulate a current flowing through the p-channel 63 between the source 56 and the drain 58. The passivation layer 72 may comprise any one of a variety of different materials to facilitate sensitivity to particular ions; for example, passivation layers comprising silicon nitride or silicon oxynitride generally provide sensitivity to hydrogen ion concentration (pH) in the analyte solution 74, whereas passivation layers comprising polyvinyl chloride containing valinomycin provide sensitivity to potassium ion concentration in the analyte solution (materials suitable for passivation layers and sensitive to other ions such as sodium, silver, iron, bromine, iodine, calcium, and nitrate, for example, are known).

With respect to ion sensitivity, an electric potential difference, commonly referred to as a "surface potential," arises at the solid/liquid interface of the passivation layer 72 and the analyte solution 74 as a function of the ion concentration in the sensitive area 78 due to a chemical reaction (e.g., usually involving the dissociation of oxide surface groups by the ions in the analyte solution in proximity to the sensitive area 78). This surface potential in turn affects the threshold voltage $V_{TH}$ of the ISFET; thus, it is the threshold voltage $V_{TE}$ of the ISFET that varies with changes in ion concentration in the analyte solution 74 in proximity to the sensitive area 78.

Referring again to FIG. 3, in this particular embodiment the micro-chamber 370 is formed on the ISFET 300 and the portion of the micro-chamber 370 that contains the sample 390 is positioned over the metal oxide region 360 of the ISFET 300. The micro-chamber is formed in an insulator material 380 (e.g. silicon nitride ($Si_3N_4$)). In this embodiment, the dimensions of the micro-chamber are 500 $\mu m^3$ (10×10×50 $\mu m$). As indicated in FIG. 3, the production of $H^+$ (i.e. protons) is an indication of cell division. Carbon dioxide ($CO_2$) production may also be an indication of cell metabolism. For example, the equation of aerobic respiration is $C_6H_{12}O_6+6O2 \rightarrow 6H_2O+6CO_2+ATP$. In other examples, the equation of the alcoholic fermentation of glucose is $C_6H_{12}O_6 \rightarrow 2C_2H_5OH+2CO_2+2ATP$. In a further example, the equation for lactic acid fermentation is $C_6H_{12}O_6 \rightarrow 2CH_3CHOHCOOH+2ATP$. When $CO_2$ is dissolved in water, it produces carbonic acid and the carbonic acid produces an associated pH change. The number of protons or the amount of $CO_2$ generated during metabolic processes or per cell division will vary from organism to organism, as will the time of cell division. The minimum threshold for reliable detection of the presence of a microorganism is less than 500,000 protons, and may be as low as 50,000 protons.

Cell behaviors that may be monitored by devices and methods described herein include the entire range of cell activity (respiration, growth, cell division, etc.) as well as cell response to changes in environmental conditions (e.g. temperature, pH) or changes in response due to the addition of sample constituents (e.g. antibiotics, antifungals, nutrients, etc.). Cell behaviors can be monitored using a variety of known techniques. For example, after subjecting the sample to conditions that cause the microorganisms in the sample to grow, the sample may be monitored for a change in conditions indicative of microorganism growth. As described above, one such change in conditions may be concentration of carbon dioxide detected in the chambers. Microorganism growth curves can be generated based on this data. Such curves can chart cell growth over time or values of a sample condition (e.g. $CO_2$ concentration) over time. As such data is being gathered (typically in real time) the change in growth rate or cell metabolic activity due to the addition of sample constituent (e.g. an antibiotic) can also be observed. Additionally, growth curves obtained may be compared to one or more standard growth curves of known microorganisms to identify the microorganism in the sample.

It should be noted that all or some of the methods described herein may be performed manually or in an automated manner. For example, preparation of a specimen and/or microorganisms prior to exposure to the ISFET may be accomplished through automated methods. Automated steps for sample preparation prior to analysis of assay are well known in the art and are not described in detail herein. Further, the deposition of microorganisms onto the ISFET may also be automated, as a part of automated specimen preparation or as a separate step. Again, automated equipment for introducing sample into microwells in a microtiter plate or other multi-well or multi-chamber configurations are well known to those skilled in the art and are not described in detail herein. Still further, data analysis and/or interpretation may be automated. Such automated equipment is well known to those skilled in the art. Some or all of the methods described herein may also be integrated with other automated analytical methods.

Although the methods described herein have generally related to the analysis of clinical samples, the methods and apparatus of the current invention may be used with clinical or non-clinical samples. For example, clinical samples that may be analyzed include any type of sample typically tested in clinical or research laboratories, including, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. The sample can be cultured and a cultured sample used. On the other hand, non-clinical samples that may be tested include, but are not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, fruit juices, meat juices or washes, and shampoos and other consumer products.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention can be applied to a microorganism detection apparatus in which, for example, a collection tube with an array of chambers including ISFETs is used to determine the presence or absence of microorganisms in a sample.

The invention claimed is:

1. A method for determining the presence of a microorganism in a sample comprising:
    introducing the sample into a volume of a housing having an array of chambers disposed therein, wherein at least some of the chambers have a height of between about 5 µm and about 100 µm and an opening at the top thereof that is from about 5 µm to about 10 µm in width to receive from the volume at least one microorganism within the chamber, each chamber in fluid communication with the overlying housing volume, the chambers not otherwise in fluid communication with each other, and wherein the housing is a centrifugable collection tube in which the array of chambers is disposed proximate a bottom of the collection tube;
    subjecting the sample to conditions that cause at least some of the microorganisms in the sample to flow into the top opening of at least some of the chambers in the housing, wherein at least some of the chambers have an ion sensitive field-effect transistor disposed therein; and
    detecting a change in the portion of the sample disposed in the chamber indicative of at least one of the presence or absence or response of the microorganism.

2. The method of claim 1, wherein the microorganisms are caused to flow toward the array of chambers in the housing by centrifugation.

3. The method of claim 1, wherein the microorganisms are caused to flow toward the array of chambers by subjecting the sample to an electric field.

4. The method of claim 1, wherein the microorganisms are caused to flow toward the array of chambers in the housing by introducing magnetic particles or paramagnetic particles into the sample, the magnetic or paramagnetic particles being configured to attract and bind the microorganism thereto, and subjecting the sample to a magnetic field in the sample.

5. The method of claim 1, further comprising:
    adding antimicrobial agents into at least some of the chambers;
    determining the susceptibility of the microorganism to the antimicrobial agents by comparing change in the sample detected in a first chamber that contains the antimicrobial agent to a change in the sample detected in a second chamber that does not contain the antimicrobial agent.

6. The method of claim 1, further comprising:
    subjecting the sample to conditions that cause the microorganisms to grow;
    monitoring the sample for a change in conditions indicative of microorganism growth; and
    generating a growth curve of the microorganism based on the change in the sample conditions.

7. The method of claim 6, further comprising determining the identity of the microorganism by comparing the generated growth curve of the microorganism to one or more standard growth curves of known microorganisms.

8. The method of claim 7, wherein generating the growth curve of the microorganism comprises monitoring cell growth over time.

9. The method of claim 7, wherein generating the growth curve of the microorganism comprises monitoring values of a sample condition over time.

10. The method of claim 9, wherein the sample condition is carbon dioxide concentration.

11. The method of claim 6, wherein the growth curve is generated in real time.

12. The method of claim 11, further comprising:
adding a constituent to the sample;
determining a change the growth curve in response to the added constituent.

13. The method of claim 12, wherein the constituent is an antibiotic.

14. The method of claim 12, wherein the constituent is an antifungal.

15. The method of claim 12, wherein the constituent is a microorganism nutrient.

* * * * *